United States Patent [19]
Barr et al.

[11] 3,942,021
[45] Mar. 2, 1976

[54] APPARATUS FOR OPTIMIZING THE YIELD OF USABLE PIECES FROM BOARDS AND THE LIKE

[75] Inventors: Anthony J. Barr; Alexander G. Mullin, both of Raleigh, N.C.

[73] Assignee: National Association of Furniture Manufacturers, Inc., Washington, D.C.

[22] Filed: Aug. 14, 1974

[21] Appl. No.: 497,387

Related U.S. Application Data

[62] Division of Ser. No. 392,885, Aug. 30, 1973.

[52] U.S. Cl.............. 250/572; 356/200; 250/223 R; 250/234; 83/371
[51] Int. Cl.²........................................ G01N 21/32
[58] Field of Search........ 250/223 R, 562, 563, 559, 250/560, 571, 572, 234, 566, 568; 356/200, 237; 83/365, 371

[56] References Cited
UNITED STATES PATENTS

| | | | |
|---|---|---|---|
| 3,274,390 | 9/1966 | Umbel | 250/555 |
| 3,329,181 | 7/1967 | Buss et al. | 83/371 X |
| 3,410,643 | 11/1968 | Jorgensen | 356/200 |
| 3,619,578 | 11/1971 | George | 250/562 X |
| 3,737,666 | 6/1973 | Dutro | 250/223 R |

*Primary Examiner*—Walter Stolwein
*Attorney, Agent, or Firm*—Mason, Fenwick & Lawrence

[57] ABSTRACT

An apparatus for optimizing the yield of predetermined usable pieces from a workpiece such as a board of lumber or the like having randomly disposed defects designated on a plane surface thereof including means for scanning the workpiece to detect unusable defect containing areas on the plane surface, means for forming and storing a primary bit matrix corresponding to a pattern of scanned unusable defect containing areas, means for identifying predetermined combinable unusable defect containing areas and predetermined combinable unusable non-defect containing areas on the primary bit matrix, means for merging identified combinable unusable defect and non-defect containing areas to produce a list defining a pattern consisting of one or a combination of a group consisting of combined and uncombined unusable areas, defining usable areas, means for establishing and storing predetermined billing requirements, means for successively determining on the basis of the usable area information and the predetermined billing requirements, various cutting patterns for the workpiece, means for selecting the cutting pattern which is determined to produce the optimum yield for the workpiece in accordance with the billing requirements, and means for dividing the workpiece in accordance with the selected cutting pattern.

11 Claims, 11 Drawing Figures

Fig-2

APPARATUS FOR OPTIMIZING THE YIELD OF USABLE PIECES FROM BOARDS AND THE LIKE

This is a division of application, Ser. No. 392,885 filed Aug. 30, 1973.

This invention relates to an apparatus and method for optimizing the yield of predetermined usable pieces from a workpiece such as a board of lumber or the like having randomly disposed defects. This invention further contemplates a novel unit for scanning the defects on a workpiece and marking a cutting pattern thereon.

In the prior art, there have been developed various types of systems for optimizing the yield of usable pieces from various types of workpieces such as boards of lumber, sheets of glass and the like having randomly disposed defects. Each of such systems basically has included a scanner for detecting the coordinates of the defects relative to a reference axis, a computer which receives input data from the scanner and selects a cutting pattern for optimizing to certain degrees the yield of usable pieces from the workpiece, and various devices controlled by the computer for marking, cutting or otherwise treating the workpiece in accordance with the particular cutting pattern selected by the computer. Usually, such systems either are elaborate in design requiring a comparatively high capital investment which are operable to provide optimum cutting patterns or are substantially less elaborate in design requiring a comparatively lesser amount of capital investment which are operable to compute and designate cutting patterns which result in substantially less than an optimum yield of usable pieces from the workpieces being processed. It thus has been found to be desirable to provide a system or an apparatus for determining and designating a cutting pattern for workpieces having randomly disposed defects which is simple in design requiring a comparatively small capital investment and yet capable of determining and designating marking, cutting or other patterns for workpieces being processed, providing optimum yields.

Accordingly, it is the principal object of this invention to provide a novel apparatus and method for optimizing the yield of usable pieces from a workpiece such as a board of lumber, sheet of glass and the like having randomly disposed defects.

Another object of the present invention is to provide a novel apparatus and method for determining and designating a marking, cutting or other form of pattern for a workpiece having randomly disposed defects which provides an optimum yield of usable pieces.

A further object of the present invention is to provide a novel system or apparatus which is comparatively simple in design and requires a relatively small capital investment, and yet which is operable to determine and designate a cutting pattern for a workpiece having randomly disposed defects to provide an optimum yield of usable pieces from workpieces being processed.

A still further object of the present invention is to provide a novel system or apparatus for determining and designating a marking, cutting or other form of pattern for a workpiece having randomly disposed defects to provide an optimum yield of usable pieces from such workpiece, which utilizes a computer having limited storage and processing capabilities.

Another object of the present invention is to provide a novel scanning unit.

A further object of the present invention is to provide a novel scanning unit capable of sensing the coordinates of defects randomly disposed on a workpiece.

A still further object of the present invention is to provide a novel scanning unit which is capable of sensing defect designating indicia applied to a workpiece being processed.

Another object of the present invention is to provide a novel unit for scanning and marking a workpiece being processed.

A further object of the present invention is to provide a novel unit for sensing defect designating indicia applied to a workpiece being processed, and marking a selected cutting pattern of said workpiece.

A still further object of the present invention is to provide a novel scanning unit for sensing defect designating indicia on a workpiece being processed which has a high degree of reading sensitivity.

Other objects and advantages of the invention will become more apparent to those persons having ordinary skill in the art to which the invention pertains, from the following description taken in conjunction with the accompanying drawings wherein:

Figure 1:
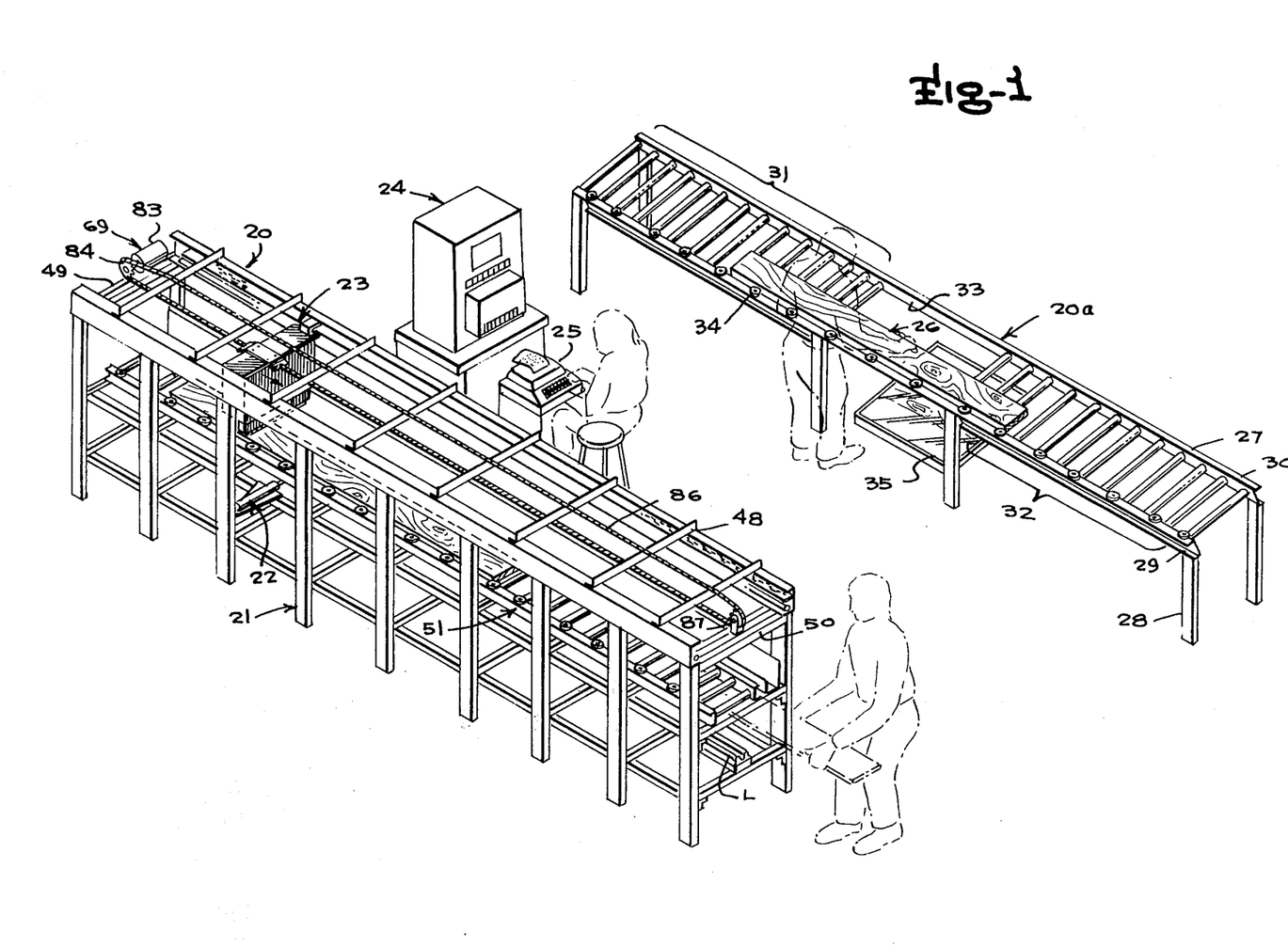
FIG. 1 is a perspective view of a system embodying the invention.
Figure 2:
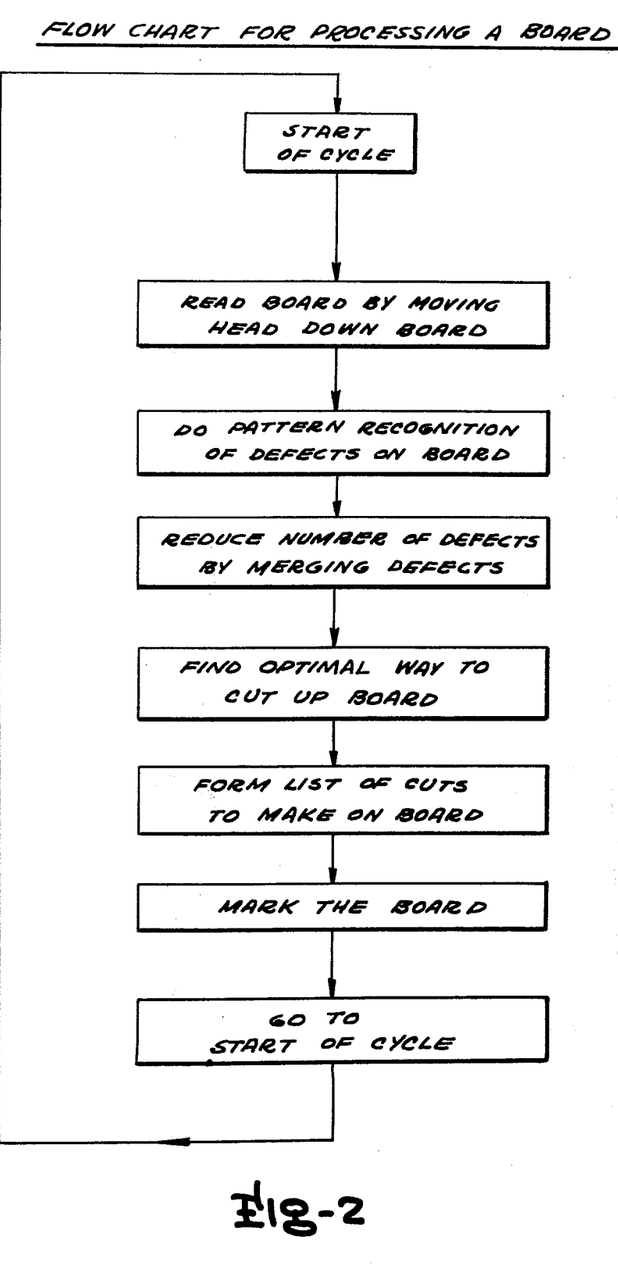
FIG. 2 is a flow diagram of the method practiced on the embodiment illustrated in FIG. 1.

Referring to the drawings, there is illustrated a system or apparatus 20, embodying the invention, which includes a support frame assembly 21, a workpiece positioning assembly 22 mounted on the frame assembly, a scanner-marker unit 23 also mounted on the frame assembly, a computer 24 operatively connected to the positioning assembly and scanner-marker unit, a terminal keyboard unit 25 operatively connected to the computer, and a separate assembly 20a for visibly detecting and marking randomly disposed defects on a workpiece to be processed by the apparatus 20, such as a board of lumber designated by the referenced numeral 26. The assembly 20a includes a roller conveyor 27 supported substantially horizontally on a plurality of legs 28. The conveyor 27 consists of a pair of side rails 29 and 30 interconnected by two spaced sets of rollers 31 and 32 providing a center opening 33 in the roller conveyor. The side rail 29 adjacent the work station of the operator is provided with a plurality of longitudinally spaced rollers 34 which are engaged by a side edge of the workpiece 26 to guide the workpiece along the length of the conveyor. Disposed below conveyor 27 in vertical alignment with opening 33 is a mirror unit 35 which provides the operator with a view of the bottom side of the workpiece disposed at the work station.

Figure 3:
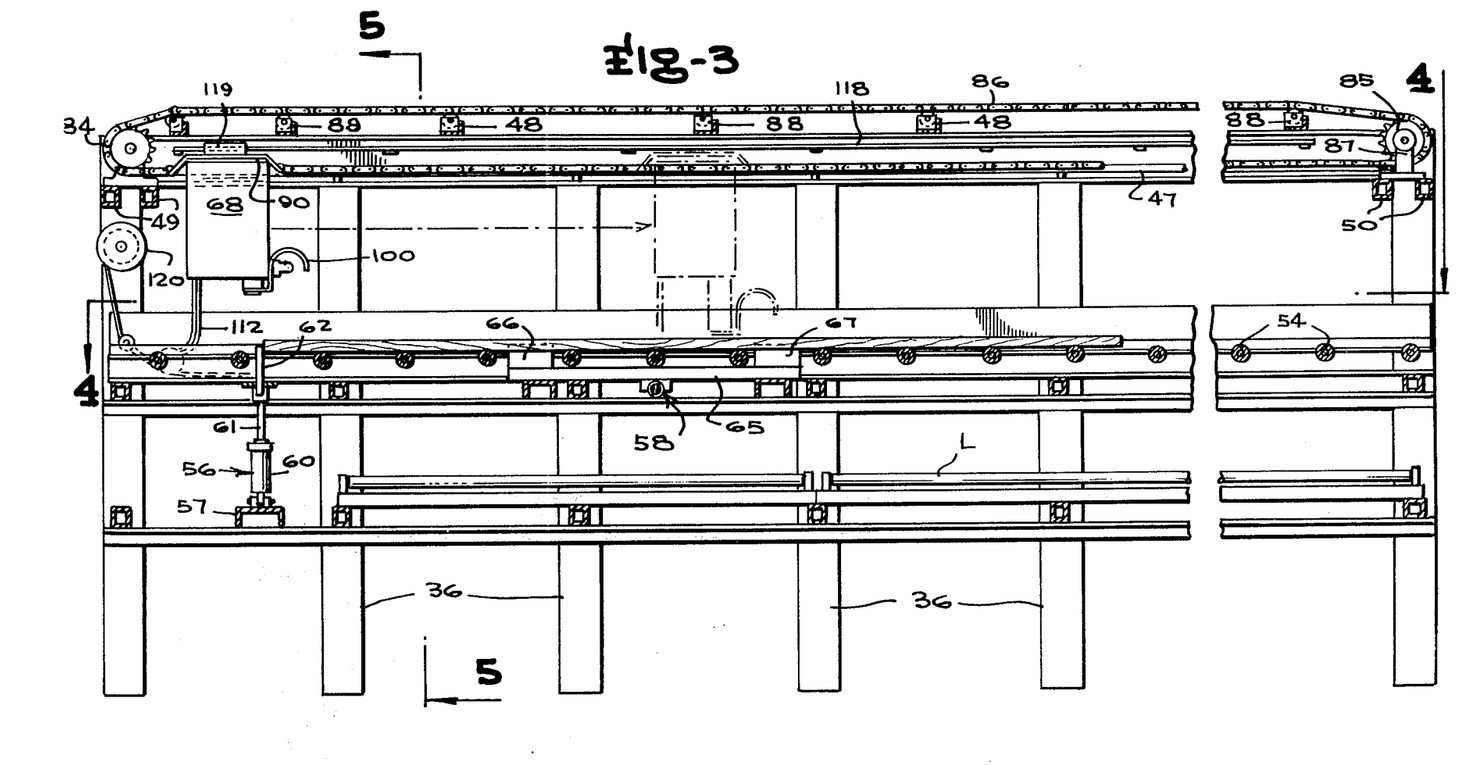
FIG. 3 is a side elevational view of the support frame assembly and scanner-marker unit of the embodiment illustrated in FIG. 1, having a portion thereof broken away.

Support frame assembly 21 generally includes a first set of longitudinally spaced post members 36, a second set of longitudinally spaced post members 37, a pair of longitudinally disposed support members 38 and 39 rigidly secured to the transversely spaced sets of post members 36 and 37 and a second pair of longitudinally disposed members 40 and 41 also rigidly secured to the sets of post members 36 and 37 and being disposed above longitudinal members 38 and 39. Rigidly connecting the sets of post members and resting on longitudinal members 38 and 39 is a set of longitudinally spaced, transversely disposed cross-piece members 42. Similarly, a set of cross-piece members 43 rigidly interconnect the sets of post members and are seated on longitudinal members 40 and 41.

Figure 5:
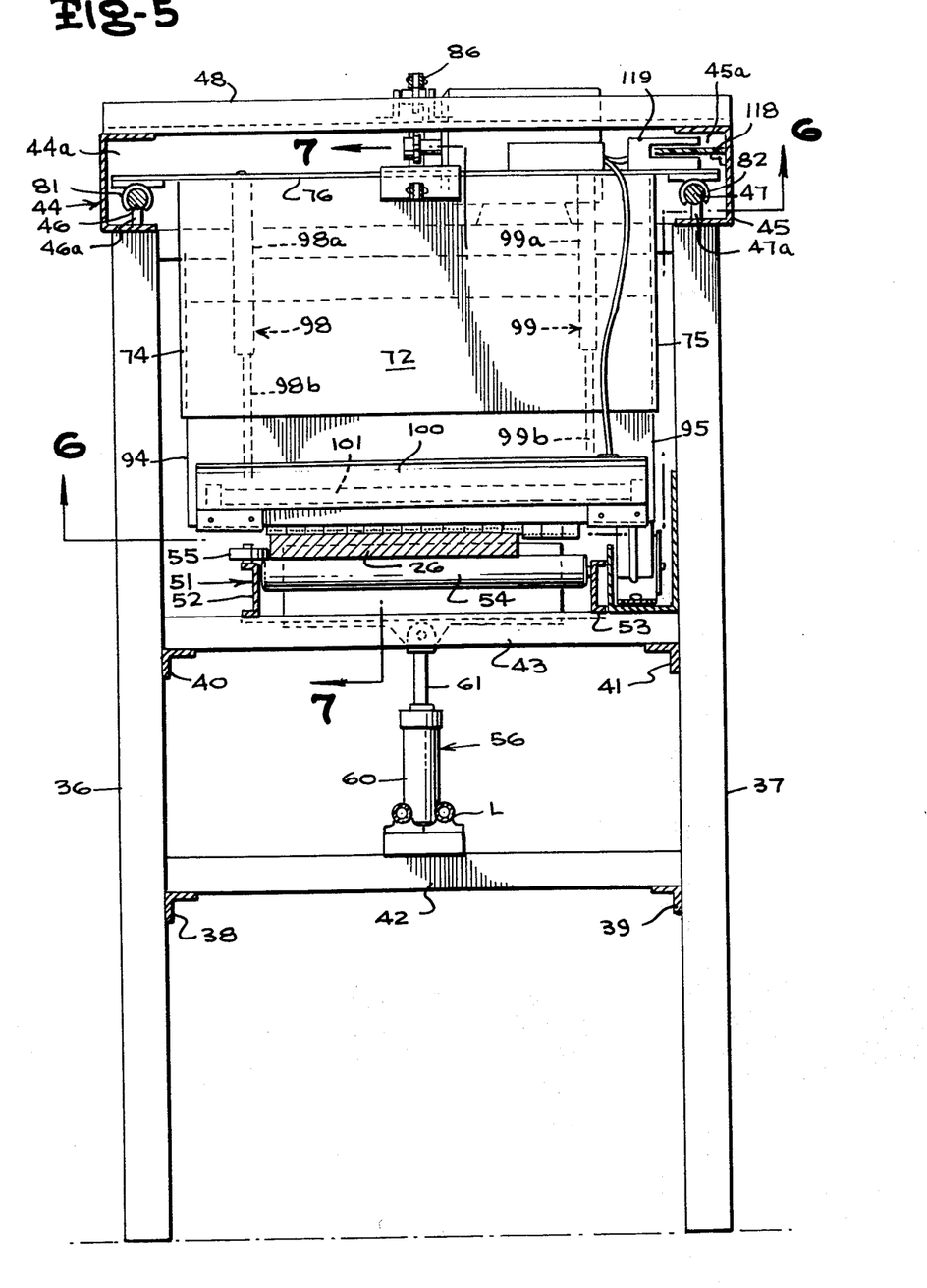
FIG. 5 is an enlarged cross-sectional view taken along line 5—5 in FIG. 3.

Seated on the upper ends of the sets of post members is a pair of longitudinally disposed, inwardly opening channel shaped guide members 44 and 45. As best illustrated in FIG. 5, the channel shaped guide members include bottom flanges rigidly secured to the upper ends of post members 36 and 37, vertically disposed web sections and inwardly projecting upper flange portions which define a pair of longitudinally disposed, inwardly opening guide channels 44a and 45a. Disposed within guide channels 44a and 45a, is a pair of longitudinally disposed guide rails 46 and 47 which are supported on a plurality of support legs 46a and 47a secured to the lower flanges of guide members 44 and 45. As will be described later, the scanner-marker unit 23 is supported on and guided along guide rails 46 and 47. Guide members 44 and 45 further are rigidly interconnected by a set of longitudinally spaced, cross-piece members 48. In addition, the end sets of post members are rigidly interconnected by sets of cross-piece members 49 and 50 which are disposed below the plane of the lower flanges of guide members 44 and 45 and which support portions of the drive assembly for the scanner-marker unit, as later will be described.

A roller conveyor 51 is supported on the upper set of cross-piece members 43 between the sets of post members 36 and 37. The conveyor generally consists of a pair of longitudinally disposed, transversely spaced channel-shaped members 52 and 53 rigidly secured to cross-piece members 43, a plurality of transversely disposed rollers 54 mounted on the side rail members 52 and 53 on which a workpiece 26 is supported for processing, and a plurality of longitudinally spaced guide rollers 55 mounted on the upper flange of side rail member 52, which are engagable by a longitudinal edge of a workpiece 26 supported on rollers 54.

Figure 4:
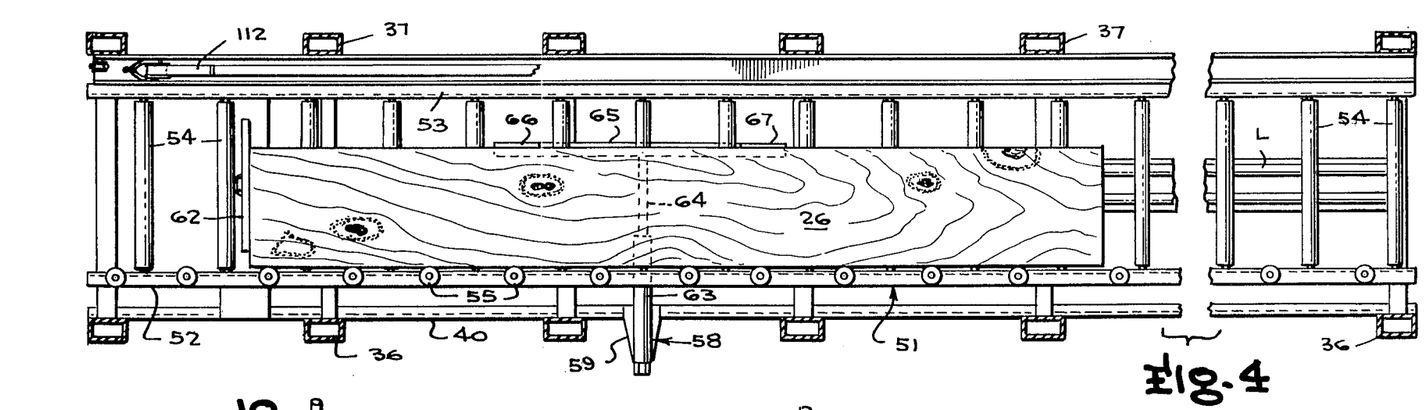
FIG. 4 is a cross-sectional view taken along line 4—4 in FIG. 3.

The workpiece positioning assembly 22 is best illustrated in FIGS. 3 and 4 and consists primarily of an end stop mechanism 56 mounted on a cross-piece member 57 supported on longitudinally disposed members 38 and 39, and a clamping mechanism 58 mounted on a bracket 59 which is rigidly secured to frame member 40. The end stop mechanism 56 consists of a vertically disposed fluid actuated piston and cylinder assembly including a cylinder 60 rigidly mounted at its lower end on cross-piece member 57 and a piston 61, and a transversely disposed abutment plate 62 mounted on the end of the piston 61. It will be appreciated that the mechanism 56 can be operated to extend piston 61 as illustrated in FIG. 3 so that the leading end of a workpiece 26 will engage plate 62 to position the workpiece longitudinally on roller conveyor 51, and piston 61 may be retracted to move plate 62 below the lower surface of the workpiece to permit the workpiece to be advanced along conveyor 51.

Clamping mechanism 58 consists of a transversely disposed fluid actuated cylinder and piston assembly including a cylinder 63 connected at its outer end to mounting bracket 59 and a piston 64 disposed below the support plane of the workpiece, and a longitudinally disposed member 65 rigidly connected intermediate its ends to the end of piston 64, having upwardly projecting clamp portions 66 and 67 which extend above the support plane of a workpiece supported on conveyor 51. It will be seen that when piston 64 is retracted, clamping portions 66 and 67 will engage a longitudinal edge of a workpiece and move it into clamping relation with the plurality of guide rollers 55 on conveyor 51 to position the workpiece transversely. The workpiece may be released merely by extending piston 64.

The operation of end stop mechanism 56 and clamping mechanism 58 is controlled by computer 24 which is responsive to various microswitches mounted on the support frame assembly for sensing the position of the workpiece on conveyor 51. It will be appreciated that when the workpiece is positioned on conveyor 51 with the leading end thereof engaging stop plate 62 and the longitudinal side edges thereof clamped between clamp portions 66 and 67 and guide rollers 55, the workpiece will be positioned for scanning by the scanner-marker unit with the leading edge thereof lying along a y-axis and the longitudinal edge thereof engaging guide rollers 55 lying along an x-axis of a pair of coordinate reference axes.

Figure 6:
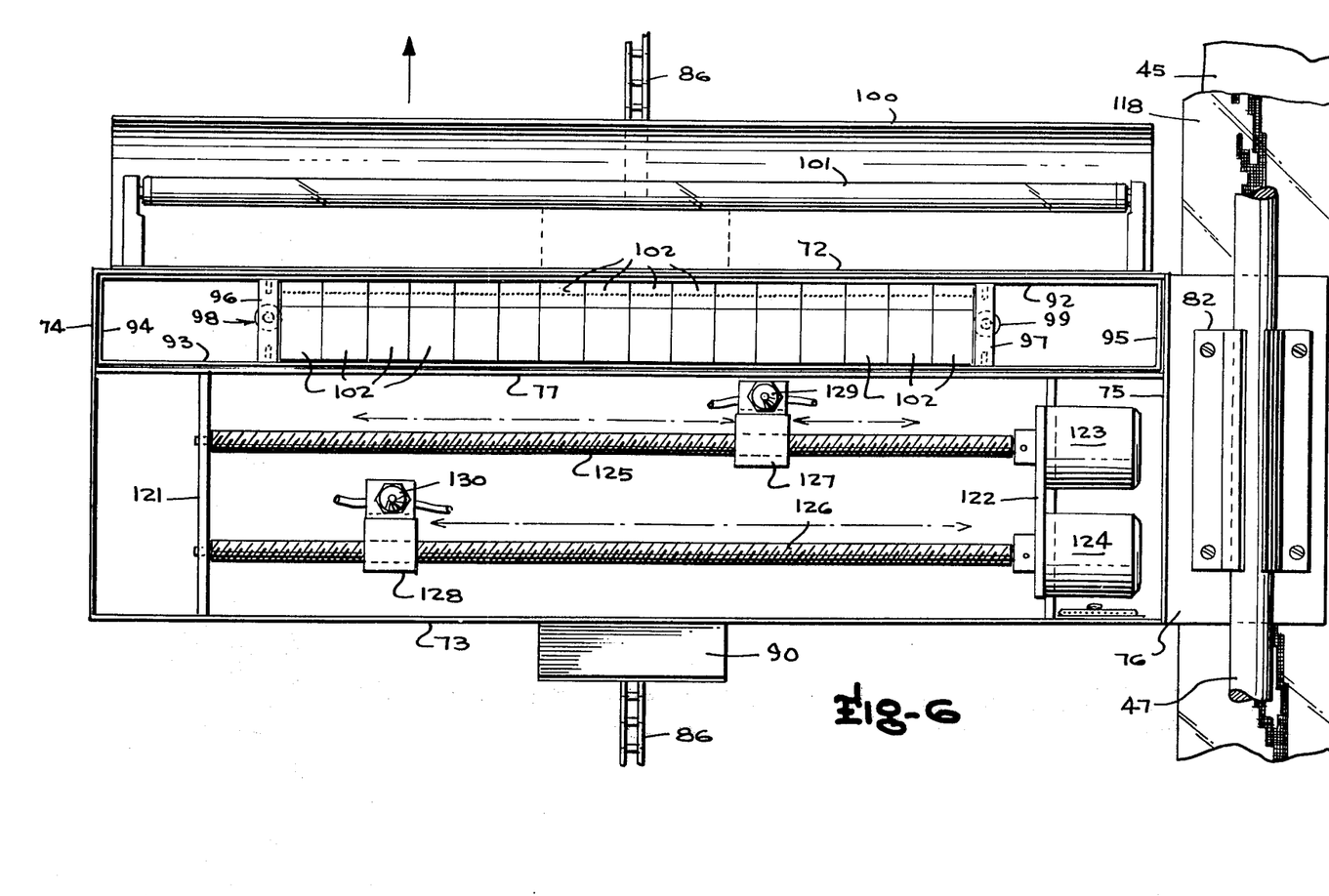
FIG. 6 is an enlarged cross-sectional view taken along line 6—6 in FIG. 5.
Figure 7:
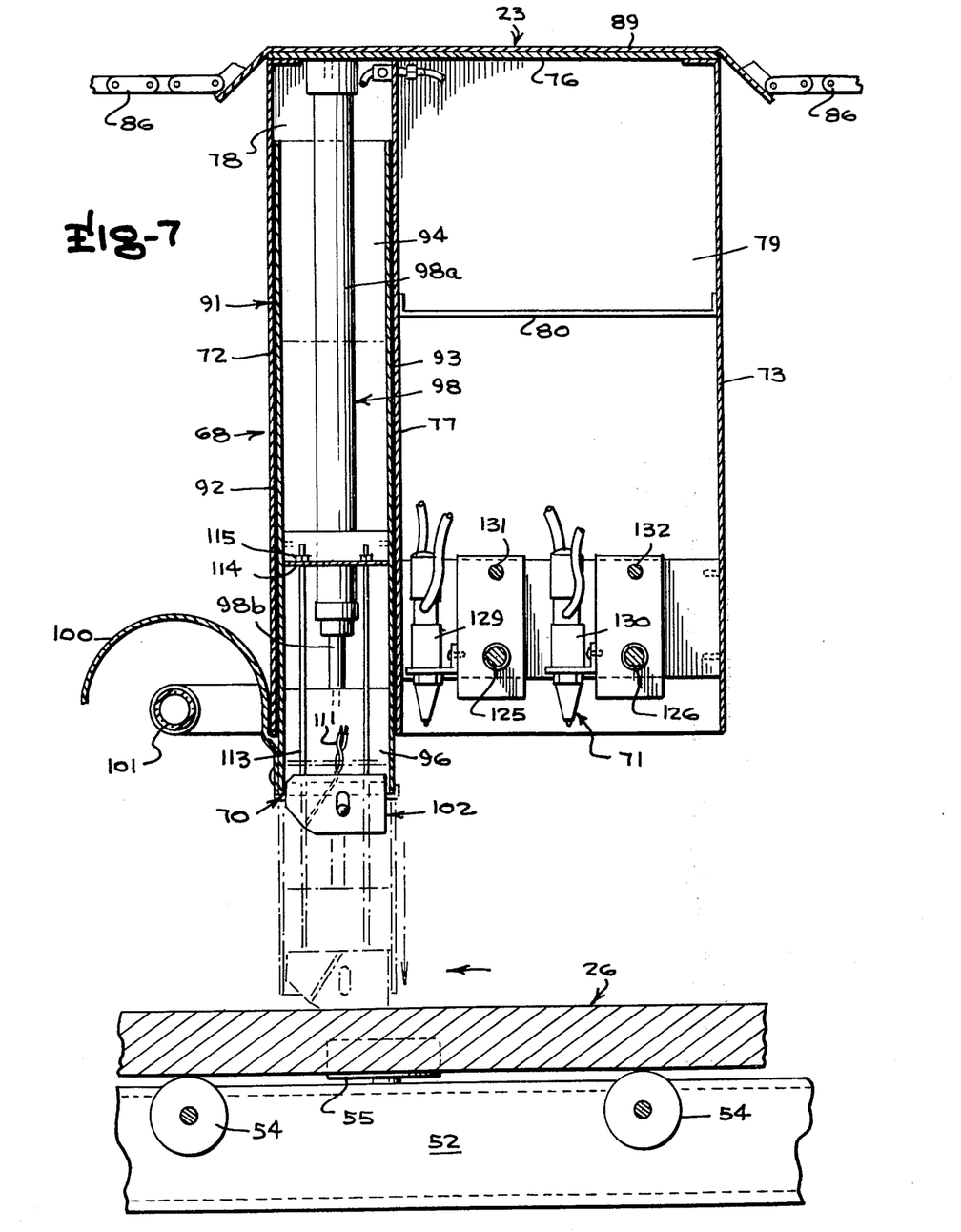
FIG. 7 is an enlarged cross-sectional view taken along line 7—7 in FIG. 5.

The scanner-marker unit 23 generally includes a carrier assembly 68 mounted on the support frame assembly, a drive assembly 69 mounted on the support frame assembly operatively connected to the carrier assembly, a scanning assembly 70 mounted on the carrier assembly and a marking assembly 71 also mounted on the carrier assembly. As best illustrated in FIGS. 5 through 7, the carrier assembly includes a housing provided with a transverse end panel 72, a transverse end panel 73 spaced longitudinally from panel 72, a pair of longitudinal side walls 74 and 75 interconnecting the end panels and a top panel 76. The housing further is provided with a transverse partition panel 77 spaced from end panel 72 to provide a compartment 78 for housing the scanning assembly 70 and a compartment 79 for housing marking assembly 71 in the lower end thereof. A longitudinal reinforcing panel 80 is provided in the upper end of compartment 79 having the flanged edges thereof rigidly secured to partition panel 77, end panel 73 and side panels 74 and 75.

As best illustrated in FIGS. 5 and 7, the lower edge of the carrier assembly terminates well above the height of a workpiece supported on conveyor 51 so that at no time during the operation of the apparatus while the scanner-marker unit is moved along the length of the workpiece, does the carrier assembly engage the workpiece. It further will be noted that, as illustrated in more detail in FIGS. 5 and 7, the side edges of top wall 76 project laterally into channels 44a and 45b and are provided with split bearing members 81 and 82 which engage guide rails 46 and 47 for supporting the scanner-marker unit on the support frame assembly and guiding it longitudinally along the length of a workpiece supported on conveyor 51.

The scanner-marker unit is adapted to be displaced along the length of a workpiece positioned on conveyor 51 by means of drive assembly 69 which includes a drive motor 83 provided with a drive sprocket 84, an idler sprocket 85 and a drive chain 86. Drive motor 83 is rigidly mounted on cross-piece members 49 so that drive sprocket 84 lies in a vertical plane passing through the longitudinal center line of the support apparatus. A bracket 87 supporting idler sprocket 85 is mounted on cross-piece members 50 so that idler sprocket 85 is aligned transversely with drive sprocket 84. Drive chain 86 is trained around sprockets 84 and 85 so that the upper flight thereof is guided along rollers 88 mounted on cross-piece members 48 and the lower flight thereof is disposed below cross-piece members 48, having the free ends thereof connected to a longitudinally disposed rigid strap 89 secured to top wall 76 of the carrier assembly. It thus will be appreciated that upon operation of drive motor 83, the scanner-marker unit 23 may be displaced along the length of a workpiece positioned on conveyor 51. The operation and speed of drive motor 83 is controlled by the computer. Generally, drive motor 83 is adapted to be driven at a relatively low speed for moving the marker-scanner unit along the length of a workpiece during the scanning phase of the operation and at a relatively high speed for positioning the scanner-marker unit during the marking phase of the operation and also in returning the unit to its starting position.

Referring to FIGS. 6 and 7, scanner assembly 70 is provided with a housing 91 which is movable vertically in compartment 78 of the carrier assembly. Housing 91 includes a pair of transverse walls 92 and 93 disposed adjacent carrier assembly panels 72 and 77, respectively, and a pair of longitudinal walls 94 and 95 which are disposed adjacent carrier assembly panels 74 and 75. Disposed at the lower end of housing 91 and rigidly secured to walls 92 and 93, inwardly from side walls 94 and 95, is a pair of longitudinally disposed brackets 96 and 97. Housing 91 and correspondingly scanning assembly 70 is displaced vertically by means of a pair of air actuated cylinder and piston assemblies 98 and 99 disposed within compartment 78, having the upper ends of the cylinder portions 98a and 99a rigidly secured to top panel 76 of the carrier assembly and the lower free ends of piston portions 98b and 99b secured to brackets 96 and 97, respectively.

Figures 8, 9, 10:
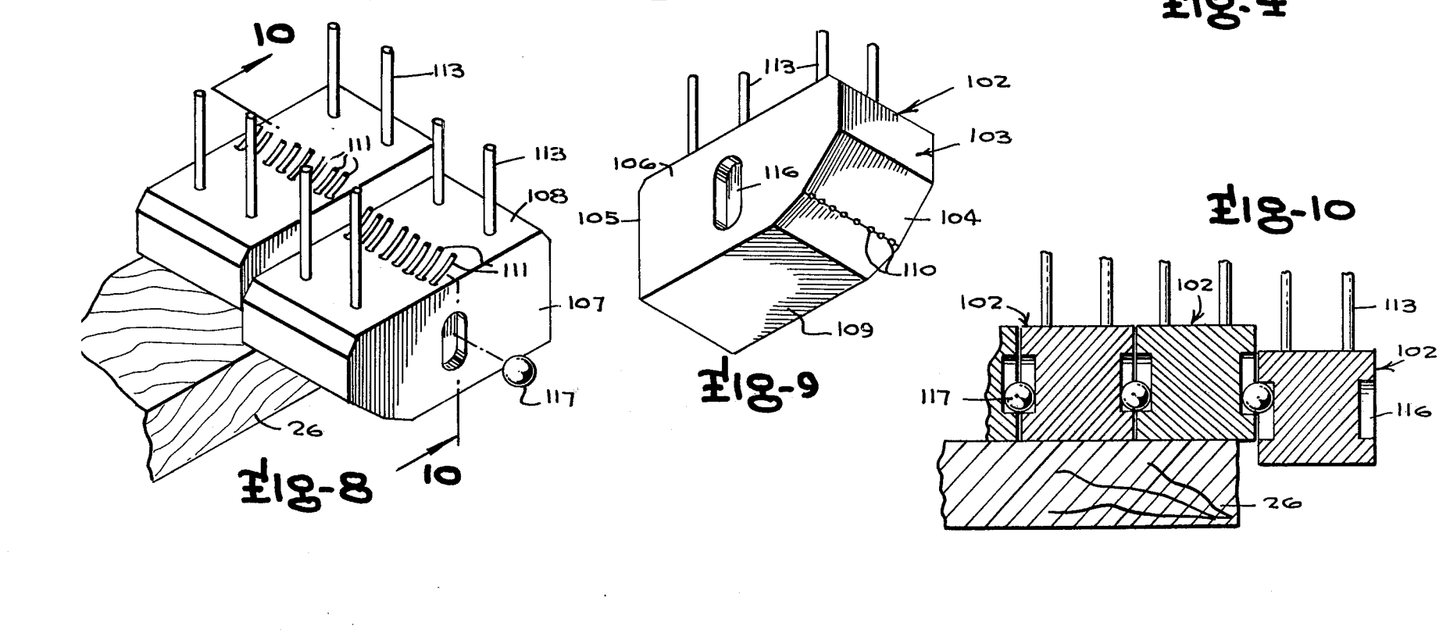
FIG. 8 is an enlarged perspective view of a pair of reading heads of the scanner-marker unit of the embodiment illustrated in FIG. 1.
FIG. 9 is a perspective view of one of the reading heads illustrated in FIG. 8, taken from a different angle.
FIG. 10 is a cross-sectional view taken along line 10—10 in FIG. 8.

A curved reflector 100 is mounted on the lower outer side of carrier assembly panel 72 which partially houses and supports a lamp 101 for illuminating workpiece 26 positioned on conveyor 51. The lamp may be of any conventional type such as an ultraviolet lamp and the like which is adapted to emit a light which will be reflected from defect designating indicia applied to the upper surface of workpiece 26 to activate the photosensitive cells of the scanning assembly. Disposed along the lower open end of housing 91, between brackets 96 and 97 is a bank of reading heads 102. As best illustrated in FIGS. 8 through 10, each of the reading heads is provided with a front face 103 which is relieved as at 104, a rear face 105, a pair of side surfaces 106 and 107, and upper and lower surfaces 108 and 109. The relieved portion 104 of each reading head is provided with a plurality of transversely spaced openings 110 in which photosensitive cells are mounted. Leads 111 from the photosensitive cells extend through the upper surface 108 and are electrically connected to an electrical lead carrier 112, shown in FIG. 3, which in turn is connected to an interface of the computer. Each of the reading heads is supported by a plurality of vertically disposed rods 113 which extend upwardly through openings in a platform panel 114 secured to panels 92 and 93 of scanning assembly housing 91. The upper ends of rods 113 are provided with nuts 115 which permit reading heads 102 to be displaced upwardly relative to housing 91 when the scanning assembly is moved to a lower operating position and reading heads 102 engage the upper surface of a workpiece 26, thus permitting the reading heads to be displaced vertically relative to housing 91 as the scanner-marker unit is moved along the workpiece during a scanning operation and correspondingly conform to any variations in height of the upper surface of the workpiece due to variations in thickness, raised projections or warpage of the workpiece. As best illustrated in FIG. 7, the length of rods 113 is adjusted so that the reading heads normally will be caused to project below the lower end of housing 91 and be permitted to be displaced upwardly into the housing while traversing the length of the workpiece during a scanning operation.

Each of the side surfaces 106 and 107 of the reading heads is provided with a vertically disposed recess 116 which registers with a similar recess in a successive reading head. Successive reading heads are provided with ball bearings 117 received within adjacent recesses 116 which function to limit the vertical displacement of successive reading heads.

The upper and lower ends of air cylinders 98a and 99a are connected through appropriate valving to a supply of compressed air. Such valves are operated by solenoids controlled by computer output signals. In operation, by appropriate computer command signals to the valve solenoids, air under pressure will be supplied selectively to the upper or lower ends of air cylinders 98a and 99a to correspondingly move the scanning assembly into and out of engagement with workpiece 26. Under such conditions, reading heads 102 will engage the workpiece, lamp 101 will be disposed immediately forwardly of the reading heads to illuminate defect designating indicia applied to the upper surface of the workpiece which will be sensed by the photosensitive cells mounted in the reading heads and the reflector 100 will function to focus light emitted by lamp 101 on the workpiece surface immediately forwardly of the reading heads and shield the workpiece surface being read by the reading heads from extraneous light. As the scanner-marker unit traverses the length of the workpiece and variations in height of the upper surface of the workpiece are encountered, the reading heads will be permitted to be displaced upwardly to continuously conform to the workpiece surface being scanned.

Seated on the center of cross-piece members 42 is a pair of longitudinally disposed lamps L, as best seen in FIGS. 1, 3 and 5. The lamps may be of any conventional type such as fluorescent adapted to emit light sufficient to activate the photosensitive cells of the scanning assembly when there is no intervening board.

The position of the scanner-marker unit along the length of a workpiece being processed, is determined from a coded reference scale disposed longitudinally along guide channel 45a, as best seen in FIG. 5. Reference scale 118 is read by a reading head 119 mounted on top wall 76 of the carrier assembly. Reading head 119 functions similarly to reading heads 102 and generates an output signal to an appropriate interface of the computer via the electrical lead carrier 112. As best illustrated in FIG. 3, the electrical lead carrier is adapted to be played out or taken up by a spring loaded reel 120 mounted at an end of the support frame assembly.

Marker assembly 71 is mounted in the lower end of compartment 79 of the carrier assembly and includes a pair of transversely spaced brackets 121 and 122 which are secured to panels 73 and 77. Mounted on bracket 122 is a pair of positioning motors 123 and 124 provided with transversely disposed, threaded drive members 125 and 126 having the free ends thereof journaled in bracket 121. Identically mounted on threaded members 125 and 126 are carrier blocks 127 and 128 on which there are mounted vertically disposed marking pens 129 and 130. The upper ends of carrier blocks 127 and 128 are mounted on guide rods 131 and 132 for maintaining marking pens 129 and 130 vertical.

Marking pens 129 and 130 are of the air brush type, being provided with an ink supply line and an air pressure line both of which are provided with appropriate valving controlled by the computer. In addition to the supply of air and ink to marking pens 129 and 130, the operation of positioning motors 123 and 124 is controlled by the computer.

It will be appreciated that by generating appropriate command signals from the computer to the controls for the main drive motor 83, positioning motors 123 and 124 and the valves for the compressed air and ink supply lines of marking pens 129 and 130, the scanner-marker unit will be displaced longitudinally relative to the workpiece to correspondingly longitudinally displace marking pens 129 and 130, carrier blocks 127 and 128 will be displaced transversely to correspondingly transversely displace marking pens 129 and 130, and ink and compressed air will be supplied to the marking pens to correspondingly cause the marking pens to mark a desired pattern on the upper surface of workpiece 26.

Terminal keyboard unit 25 may be of any conventional, commercially available type which is capable of being operated to input desired billing requirements or cutting orders into computer 24. Primarily, the billing requirements inputted into the computer through the terminal keyboard unit consist of the desired sizes, quantities of sizes and priority of pieces required, usually for a production run.

Computer 24 consists of what commonly has been referred to as a "mini-computer" which has limited data storing and processing capabilities. An example of such a computer is the NOVA 800 computer manufactured by the Data General Corporation of Southboro, Massachusetts. The computer is provided with appropriate data storing components and circuitry for; storing billing requirements inputted through the terminal keyboard unit, forming and storing a primary bit matrix containing the coordinates of designated defects provided on a workpiece being processed as a result of input signals from the scanner-marker unit, identifying combinable unusable defect containing areas and combinable unusable non-defect containing areas on the primary bit matrix in accordance with a predetermined program, merging combinable unusable defect and non-defect containing areas in accordance with the program to produce a list containing the coordinates of one or a combination of a group consisting of unusable areas, defining usable areas, and selecting responsive to the stored billing requirements and the list defining unusable areas, a cutting pattern for the workpiece providing an optimum yield of usable pieces complying to at least a portion of the predetermined billing requirements. The computer further includes appropriate circuitry for transmitting command signals to main drive motor 83 for displacing the scanner-marker unit longitudinally and correspondingly positioning marking pens 129 and 130 longitudinally, to pen positioning motors 123 and 124 for positioning the pens transversely and to the solenoids operating the valves controlling the supply of compressed air and ink to the marking pens. In addition, the computer includes appropriate circuitry for reestablishing the billing requirements as the previously established billing requirements are at least partially satisfied.

Figure 11:
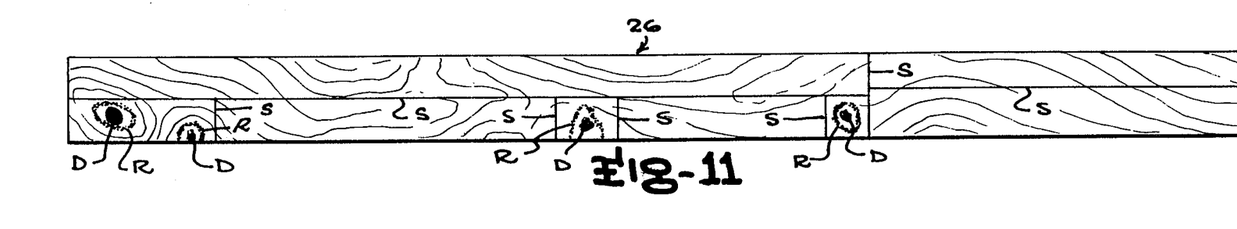
FIG. 11 is a top plan view of a board of lumber having randomly disposed defects, having been processed through the embodiment of the invention illustrated in FIGS. 1 through 10 and marked with a cutting pattern to produce an optimum yield of usable pieces.

In the operation of the system as described, assuming it is desired to mark boards of lumber of the type illustrated in FIG. 11, having randomly disposed defects D to produce an optimum yield in accordance with predetermined billing requirements, initially computer 24 is programmed to perform the aforementioned functions and the billing requirements are inputted into the computer by means of terminal keyboard unit 25. The board is then placed on roller conveyor 27 of assembly 20a so that a longitudinal edge of the board engages guide rollers 34 and the board spans opening 33. With the board thus positioned so that an operator may view any defects on the bottom side of the board on mirror unit 35, a worker encircles on the upper side of the board each defect containing area with a light reflecting material as denoted by the reference letter R in FIG. 11. When all of the defects on the upper and lower surfaces of the board are designated on the upper surface thereof, the board either is stacked for further processing through system 20 or is carried directly to apparatus 20 for further processing.

Boards containing defect designating markings are processed through apparatus 20 by initially inserting each board through one end of the apparatus onto roller conveyor 51 as illustrated in FIG. 1. The operator then positions the board against guide rollers 55 and moves the board toward the opposite end thereof until the leading edge of the board engages stop plate 62. As the board is moved toward stop plate 62, certain microswitches are tripped which energize appropriate circuitry in computer 24 to actuate end stop mechanism 56 and clamping mechanism 58 in a predetermined sequence. Initially, the leading edge of the board engages stop plate 62 to position the leading edge of the board along a y-axis and then clamping mechanism 58 is actuated to cause clamping plates 66 and 67 to engage a longitudinal edge of the board and move the opposite longitudinal edge of the board against guide rollers 55 so that the roller engaging edge will be disposed along an x-axis of the predetermined coordinate reference axes. In such position, with the leading edge disposed along the y-axis and one of the longitudinal edges disposed along the x-axis of the coordinate reference axes, the board is properly positioned for scanning. The proper positioning of the board is signaled to the computer which responds by transmitting a command signal to main drive motor 83 to begin the scanning phase of the operation.

Normally, scanner-marker unit 23 will be in the position as illustrated in FIGS. 1 and 3 with the carrier assembly 68 disposed adjacent the leading edge of the board to be processed and the scanner assembly of its elevated or retracted position. Preceeding energization of main drive motor 83 for displacing carrier assembly 68 along the length of the positioned workpiece, the computer transmits a command signal to the solenoids operating the valves supplying fluid under pressure to air cylinders 98a and 99a to cause pistons 98b and 99b to extend and correspondingly move the bank of reading heads 102 into engagement with the upper surface of the workpiece. Simultaneously, lamp 101 will be energized to illuminate the upper surface of the board.

As carrier unit 68 is moved along the length of the workpiece, light emitted from lamp 101 and reflected by defect designating indicia R and light emitted from lamps L in the areas not covered by the board will be sensed by the photosensitive cells in the reading heads. As the photosensitive cells are thus activated by the reflected light, they operate to generate signals which are amplified and transmitted to the computer. Simultaneously, reading head 119 reads coded reference scale 118 and similarly transmits a signal to the computer. It will be appreciated that the signals transmitted by the reading heads 102 and 119 indicate to the computer the $x$ and $y$ coordinates of the defect containing areas of the board being processed and of the scanned areas not covered by the board which appear as defects because of the light emitted from lamps L. As previously mentioned, the computer produces and stores a primary bit matrix responsive to the input signals from reading heads 102 and 119, corresponding to the pattern of defect containing areas sensed on the board being processed. In the event any of reading heads 102 encounters any variation in height of the upper surface of the board which may be the result of variations in thickness of the board or warpage, the reading head will be permitted to be displaced vertically relative to successive reading heads to conform to any such variation in height. It further will be noted that due to the proximity of lamp 101 to reading heads 102, the focusing of light onto the area being scanned immediately forwardly of the reading heads, and the shielding of the area being scanned from extraneous light, an accurate reading of the defects on the workpiece is achieved. As soon as the carrier assembly has traversed the full length of the workpiece and the reading heads drop off the end of the board, the computer causes appropriate command signals to be transmitted to stop the main drive motor, deenergize lamp 101 and lifting or retracting the scanner assembly. The main drive motor is then operated to return the carriage assembly to a position adjacent the leading edge of the workpiece, in position to begin the marking phase of the operation.

As soon as the primary bit matrix has been formed and stored by the computer, the computer next operates to scan the primary bit matrix for predetermined combinable unusable defect containing areas and combinable unusable non-defect containing areas. Such combinable unusable defect and non-defect containing areas then are merged to produce a list of unusable areas around which usable pieces may be cut. The computer then functions, responsive to the stored billing requirements and the usable areas defined by the list, to select, in accordance with the selected program, a cutting pattern for the board providing an optimum yield of usable pieces complying with at least a portion of the billing requirements. In this regard, it will be appreciated that by merging unusable defect and non-defect containing areas, the number of unusable areas on the list is reduced thus correspondingly decreasing the number of combinations required to be analyzed by the computer.

Once the cutting pattern for the board being processed has been selected by the computer, command signals are transmitted by the computer to main drive motor 83 and pen positioning motors 123 and 124 to position the marking pens. Simultaneously, command signals are transmitted to the marking pen controls so that the pens will operate to mark the selected cutting pattern on the workpiece, consisting of a combination of cross-cut and ripping lines designated by the reference letter S in FIG. 11. When the carrier assembly reaches the full length of its travel, such condition is sensed by the computer which then operates to return the carrier assembly to its start position and actuate mechanisms 56 and 58 to release the workpiece and permit it to be removed.

The apparatus as described can be modified so that once the cutting pattern has been selected, in lieu of transmitting command signals to the main drive motor and pen positioning motors to position and operate the marking pens, such signals could function to operate an apparatus for cutting the boards.

From the foregoing detailed description, it will be evident that there are a number of changes, adaptations and modifications of the present invention which come within the province of those skilled in the art. However, it is intended that all such variations not departing from the spirit of the invention be considered as within the scope thereof and as limited solely by the appended claims.

We claim:

1. In an apparatus for optimizing the yield of predetermined usable pieces from a workpiece such as a board of lumber or the like having randomly disposed defects in at least one plane surface thereof, a scanning unit including a carrier assembly, means for illuminating defect designating indicia applied to the plane surface of said workpiece, a plurality of transversely disposed reading heads mounted on said carrier assembly and means mounted on said carrier assembly for moving said plurality of reading heads selectively into and out of engagement with said plane surface, each of said reading heads having a plurality of transversely disposed photosensitive cells for detecting said indicia and for providing signals which form a primary bit matrix corresponding to the scanned defect designating indicia, said reading heads being displaceable vertically relative to successive reading heads to permit the position of each reading head to adjust vertically and conform to any variations in thickness of said workpiece as said scanning unit traverses the length thereof.

2. A scanning unit according to claim 1 wherein lower leading edges of said reading heads are relieved and said photosensitive cells are disposed within said relieved surfaces.

3. A scanning unit according to claim 1 including means interengaging successive reading heads for limiting vertical displacement therebetween.

4. A scanning apparatus according to claim 1 including means for reading a coded reference scale disposed on said apparatus.

5. In an apparatus for optimizing the yield of predetermined usable pieces from a workpiece such as a board of lumber or the like having randomly disposed defects in at least one plane surface thereof, a scanner-marker unit comprising a carrier assembly movable relative to said workpiece along the length thereof, means mounted on said carrier assembly for detecting defects on said workpiece and means mounted on said carrier assembly for marking cutting lines on said workpiece, said defect detecting means including means for illuminating defect designating indicia applied to a plane surface of said workpiece, a plurality of transversely disposed reading heads and means for moving said plurality of reading heads selectively into and out of engagement with said workpiece, each of said reading heads having a plurality of transversely disposed photosensitive cells for sensing light from said indicia and for providing signals which form a primary bit matrix corresponding to the scanned defect designating indicia, said reading heads being displaceable vertically relative to successive reading heads to permit the position of each reading head to adjust vertically and conform to any variations in thickness of said workpiece as said unit traverses the length thereof.

6. A scanner-marker unit according to claim 5 wherein lower leading edges of said reading heads are relieved and said photosensitive cells are disposed within said relieved surfaces.

7. A scanner-marker unit according to claim 5 including means interengaging successive reading heads for limiting vertical displacement therebetween.

8. A scanner-marker unit according to claim 5 wherein said detecting means includes means for reading a coded reference scale disposed on said apparatus.

9. An apparatus according to claim 5 wherein said marking means comprises at least one vertically disposed pen moveable transversely.

10. A scanner-marker unit according to claim 9 wherein said pen comprises an ink emitting air brush.

11. A scanner-marker unit according to claim 9 wherein said pen is mounted on a transversely disposed threaded drive member.

\* \* \* \* \*